US011918733B2

United States Patent
Neagos et al.

(10) Patent No.: US 11,918,733 B2
(45) Date of Patent: Mar. 5, 2024

(54) MEDICAL INSTRUMENT AND AEROSOL GENERATION DEVICE

(71) Applicant: Erbe Elektromedizin GmbH, Tuebingen (DE)

(72) Inventors: Alexander Neagos, Reutlingen (DE); Markus Enderle, Tuebingen (DE); Christian Schaefer, Kusterdingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 757 days.

(21) Appl. No.: 16/582,491

(22) Filed: Sep. 25, 2019

(65) Prior Publication Data

US 2020/0093999 A1 Mar. 26, 2020

(30) Foreign Application Priority Data

Sep. 26, 2018 (EP) ..................................... 18196941

(51) Int. Cl.
*A61M 11/02* (2006.01)
*A61B 1/313* (2006.01)
(Continued)

(52) U.S. Cl.
CPC ........... *A61M 11/02* (2013.01); *A61M 11/008* (2014.02); *A61M 11/06* (2013.01); *A61M 31/00* (2013.01); *A61B 1/3132* (2013.01)

(58) Field of Classification Search
CPC .............. A61M 11/006; A61M 11/007; A61M 11/008; A61M 11/02; A61M 11/06;
(Continued)

(56) References Cited

U.S. PATENT DOCUMENTS 2,153,240 A * 4/1939 Dailey .................. B05B 7/2445
137/553
2,177,032 A * 10/1939 Baumgardner ....... B05B 9/0838
222/323

(Continued)

FOREIGN PATENT DOCUMENTS

CN 104225705 A 12/2014
EP 0740926 A2 11/1996
(Continued)

OTHER PUBLICATIONS

Extended European Search Report dated Mar. 26, 2019, in corresponding European Patent Application No. 18196941.1 (9 pages).
(Continued)

*Primary Examiner* — Kathryn E Ditmer
(74) *Attorney, Agent, or Firm* — Fitch, Even, Tabin & Flannery LLP (57) ABSTRACT

A medical instrument with an aerosol outlet, which is fluidically connected—via an aerosol line—to a generation device. The generation device is adapted to generate aerosol for dispensing by means of the medical instrument. In addition, a generation device is stated, which, in embodiments of the generation device, for example can be used in a device with the instrument according to the invention. The generation device comprises a mixing unit for mixing a liquid and a gas together, which mixing unit is connected to a liquid container for supplying the mixing unit with a liquid, in which case the generation device is adapted to utilize the gas pressure of a gas under pressure subjecting the liquid to a pressure in order to press the liquid out of the liquid container to the mixing unit.

16 Claims, 3 Drawing Sheets

(51) Int. Cl.
*A61M 11/00* (2006.01)
*A61M 11/06* (2006.01)
*A61M 31/00* (2006.01)

(58) Field of Classification Search
CPC .... A61M 11/08; A61M 31/00; A61M 35/003; A61M 35/20; A61M 35/25; A61M 2005/14513; A61M 2005/14566; A61M 5/1483; A61M 5/1486; B65D 83/00; B65D 83/0055
See application file for complete search history.

(56) References Cited

U.S. PATENT DOCUMENTS

| | | | | |
|---|---|---|---|---|
| 2,847,249 A | * | 8/1958 | Evans | B05B 9/047 239/323 |
| 3,198,438 A | * | 8/1965 | Hultgren | B05B 7/2445 239/323 |
| 3,270,920 A | * | 9/1966 | Nessler | B05B 9/0838 222/488 |
| 3,507,278 A | * | 4/1970 | Werding | A61M 5/155 604/141 |
| 3,580,249 A | * | 5/1971 | Takaoka | A61M 11/06 239/338 |
| 3,809,080 A | * | 5/1974 | Deaton | A61M 16/125 261/78.2 |
| 3,838,794 A | * | 10/1974 | Cogley | B65D 75/38 604/141 |
| 3,949,753 A | * | 4/1976 | Dockhorn | A61M 3/022 606/79 |
| 4,048,994 A | * | 9/1977 | Lo | A61J 1/10 604/142 |
| 4,162,030 A | * | 7/1979 | Capra | B67D 1/0462 239/323 |
| 4,174,071 A | * | 11/1979 | Lau | B05B 15/00 239/365 |
| 4,215,476 A | * | 8/1980 | Armstrong | A61C 17/0208 604/32 |
| 4,376,376 A | | 3/1983 | Gregory | |
| 4,406,406 A | * | 9/1983 | Knapp | B05B 7/2445 239/323 |
| 4,551,136 A | * | 11/1985 | Mandl | A61M 5/1483 604/141 |
| 4,913,698 A | * | 4/1990 | Ito | A61M 1/85 604/35 |
| 4,974,634 A | * | 12/1990 | Agulia | B01F 25/316 137/564.5 |
| 5,074,839 A | * | 12/1991 | Choksi | A61M 1/682 604/408 |
| 5,094,269 A | * | 3/1992 | Agulia | A01C 23/042 137/564.5 |
| 5,399,159 A | * | 3/1995 | Chin | A61M 13/003 604/26 |
| 5,497,912 A | * | 3/1996 | Hoback | A61M 5/1486 604/141 |
| 5,695,653 A | * | 12/1997 | Gsell | A61M 1/02 210/252 |
| 5,720,728 A | * | 2/1998 | Ford | A61M 5/1483 604/141 |
| 5,730,731 A | * | 3/1998 | Mollenauer | A61B 1/042 604/246 |
| 5,797,520 A | * | 8/1998 | Donahue | B05B 9/047 222/394 |
| 5,951,461 A | * | 9/1999 | Nyo | A61B 1/2676 600/117 |
| 6,083,189 A | * | 7/2000 | Gonon | B67D 7/0255 604/118 |
| 6,096,007 A | * | 8/2000 | Haan | A61M 3/0245 604/113 |
| 8,945,605 B2 | | 2/2015 | Boucher et al. | |
| 2003/0155011 A1 | * | 8/2003 | Gilmore | F04F 5/24 137/268 |
| 2003/0181917 A1 | * | 9/2003 | Gertner | A61M 15/0066 604/24 |
| 2004/0154617 A1 | * | 8/2004 | Enk | A61M 16/08 128/203.12 |
| 2004/0231668 A1 | * | 11/2004 | Kates | A61M 15/0085 128/203.26 |
| 2004/0232171 A1 | * | 11/2004 | Bobst | A61M 5/1486 222/399 |
| 2006/0175433 A1 | * | 8/2006 | Escoto, Jr. | B05B 7/241 239/377 |
| 2007/0164133 A1 | * | 7/2007 | Lin | A61M 5/3007 239/525 |
| 2007/0181599 A1 | * | 8/2007 | Kosmyna | B05B 12/149 222/95 |
| 2008/0110458 A1 | | 5/2008 | Srinivasan et al. | |
| 2008/0125742 A1 | | 5/2008 | Podhajsky | |
| 2009/0050137 A1 | * | 2/2009 | Wissink | A61M 15/009 128/200.14 |
| 2009/0326621 A1 | | 12/2009 | El-Galley | |
| 2010/0059605 A1 | * | 3/2010 | Plantz | B01F 25/312 239/316 |
| 2011/0137281 A1 | * | 6/2011 | Tang | A61M 5/30 604/500 |
| 2011/0230820 A1 | * | 9/2011 | Lillis | A61M 13/00 604/24 |
| 2012/0048264 A1 | * | 3/2012 | Finlay | A61M 39/105 128/200.14 |
| 2012/0167878 A1 | * | 7/2012 | Belson | A61M 16/12 128/200.14 |
| 2012/0172789 A1 | | 7/2012 | Fischer et al. | |
| 2012/0172874 A1 | | 7/2012 | Fischer et al. | |
| 2013/0079733 A1 | * | 3/2013 | Burt | B05B 17/0607 239/102.1 |
| 2013/0200537 A1 | * | 8/2013 | Ken | B01F 23/231 261/122.1 |
| 2014/0109899 A1 | | 4/2014 | Boucher et al. | |
| 2014/0114261 A1 | * | 4/2014 | Geppert | A61M 11/00 604/290 |
| 2015/0028131 A1 | * | 1/2015 | Joseph | B05B 7/2478 239/318 |
| 2015/0040902 A1 | * | 2/2015 | Blum | A61M 16/0875 128/203.27 |
| 2015/0209545 A1 | * | 7/2015 | Houston | A61M 16/104 128/200.16 |
| 2016/0213864 A1 | * | 7/2016 | Eilat | A61M 11/001 |

FOREIGN PATENT DOCUMENTS

| | | | | |
|---|---|---|---|---|
| EP | 2338587 A1 | | 6/2011 | |
| EP | 3244820 B1 | * | 6/2020 | A61B 17/24 |
| GB | 2488992 A | * | 9/2012 | A61M 11/06 |
| JP | H08336573 A | | 12/1996 | |
| JP | 2005-262037 A | | 9/2005 | |
| JP | 2007508930 A | | 4/2007 | |
| JP | 2008-515606 A | | 5/2008 | |
| JP | 2012-223688 A | | 11/2012 | |
| JP | 2013-150987 A | | 8/2013 | |
| JP | 2014-100563 A | | 6/2014 | |
| KR | 20020022222 A | | 3/2002 | |
| TW | 200400064 A | | 1/2004 | |
| WO | 2011/029572 A1 | | 3/2011 | |
| WO | 2011/029573 A1 | | 3/2011 | |
| WO | 2016/115031 A2 | | 7/2016 | |

OTHER PUBLICATIONS

Office Action dated Jun. 15, 2022, in corresponding Russian Application No. 2019129553 (24 pages).
Office Action and Search Report dated Jul. 20, 2022 in corresponding Chinese Application No. 2019109170227, 24 pages.
China National Intellectual Property Administration; 2nd Office Action and Search Report in corresponding Chinese Application No. 2019109170227, dated Mar. 17, 2023; 10 pages.
Japan Patent Office; Notice of Reasons for Refusal in corresponding Japanese Patent Application No. 2019-173782, dated Jun. 9, 2023; 23 pages.

(56) References Cited

OTHER PUBLICATIONS

China National Intellectual Property Administration; Decision to Grant Patent in corresponding Chinese Patent Application No. 201910917022.7, dated Jul. 10, 2023; 19 pages.

* cited by examiner

MEDICAL INSTRUMENT AND AEROSOL GENERATION DEVICE

RELATED APPLICATION(S)

This application claims the benefit of European Patent Application No. 18196941.1, filed Sep. 26, 2018, the contents of which are incorporated herein by reference as if fully rewritten herein.

TECHNICAL FIELD

The invention relates to a medical instrument for the application of an aerosol, as well as to a generation device for an aerosol.

BACKGROUND

Publications WO 2011/029572 A1, as well as WO 2011/029 573 A1 have disclosed medical instruments that comprise a head on the distal end of the instrument, in which a liquid, in particular a saline solution, and a gas, for example $CO_2$, are combined for dispensing a mixture (aerosol) of liquid droplets that are finely divided in the gas with the instrument.

Publication EP 0 740 926 A2 describes a device comprising an aerosol jet formation component.

Medical instruments, in particular their heads on the distal end of the medical instruments, or applicators, frequently are intended for single use only because they need to be clean and sterile.

It is the object of the present invention to state an improved concept for an instrument for dispensing of an aerosol.

SUMMARY

This object is achieved with a medical instrument, as well as with a generation device for an aerosol as described herein.

In one aspect of the invention, a medical instrument is disclosed. The medical instrument according to the invention has an aerosol outlet for dispensing an aerosol by means of the medical instrument. By means of an aerosol line, particularly preferably an aerosol hose line (hereinafter also referred to as hose line), the instrument is fluidically connected to a generation device, which generation device is adapted to generate an aerosol, and to supply the aerosol line with an aerosol for dispensing the aerosol by means of the medical instrument. The generation device is adapted to generate the aerosol by vaporizing a liquid by means of a gas stream.

Embodiments of the medical instrument according to the invention may be, for example, instruments for open surgery or endoscopic, in particular laparoscopic, surgery.

Considering embodiments, the instrument has a handling section, which handling section has an aerosol outlet, the handling section being fluidically connected to the generation device by means of the aerosol line, for example an aerosol hose line.

For example, the handling section may be formed by an applicator or hand grip part. The handling section is adapted for guiding, controlling the medical instrument during the procedure performed with the medical instrument, and/or, for example, for orienting the aerosol outlet for the desired dispensing direction of the aerosol.

For example, the medical instrument may be a probe for dispensing an aerosol, which probe may be adapted to be arranged in the working channel of an endoscope, so that the distal end of the probe projects from the working channel on the distal end of the endoscope. The outlet may be arranged on the distal end of the probe.

The medical instrument is preferably releasably connected to the generation device in order to uncouple the medical instrument, following use, from the generation device for the aerosol in order to connect, for example, an unused medical instrument to the generation device.

The medical instrument has been simplified in so far that no separate gas and fluid lines are required for conveying gas and liquid independently of each other up to an aerosol generation unit in the instrument, for example in the handling section of the instrument. A preferably flexible aerosol line from the generation device to the instrument—in embodiments up to the handling section—is sufficient. Of course, the medical instrument may comprise additional lines, also gas or fluid lines and/or electrical lines, which may lead to the instrument—in the embodiments to a handling section—which, however preferably are not used for aerosol generation in the medical instrument, e.g., in a handling section of the medical instrument.

In contrast with an instrument with two dedicated lines to a mixing unit for the generation of the aerosol in the instrument, e.g., in or on the handling section of the instrument, it is possible to reduce development and manufacturing costs when a generation device for generating aerosol in the instrument, e.g., in or on a handling section of the instrument, is absent. Development and manufacturing costs should be particularly low for single-use products. This makes the medical instrument particularly cost-effective regarding development and manufacture. The medical instrument may be a single-use instrument.

Preferably, it is possible with the aerosol line to implement large distances between the generation device for the aerosol and the instrument, in embodiments between the generation device for the aerosol and the handling section, or between the generation device and the aerosol outlet. Preferably, the length of the aerosol line between the generation device and the aerosol outlet or the instrument is at least 1 meter, particularly preferably, at least 2 meters.

During use of the instrument, the generation device for the aerosol is preferably supported by the base, for example via a carrying device. The generation device may be carried, for example, by a carrying device which is supported by the base. Referring to such embodiments, the user of the instrument need not himself carry the weight of the generation device during the medical application of the instrument. For example, the generation device may be arranged on a device which provides an electrical HF-output to be applied to an electrode, which electrode—in the embodiments of the inventive instrument—may be arranged in or on the instrument, for example, in or on a handling section. The device may be supported by the base, for example via a carrying device.

The instrument or the handling section, if any, can preferably be moved relative to the generation device. The generation device can be uncoupled from the instrument or handling section, if any, in such a manner that the generation device is not necessarily moved along due to the movement of the instrument during the medical application. Preferably, the generation instrument is arranged on a proximal end of a device which comprises the instrument according to the invention. Alternatively or additionally, the handling section is arranged on the distal end of the device which comprises the instrument according to the invention.

A device with the instrument is particularly cost-effective, as well as particularly quietly and simply to control, when the liquid is conveyed to the generation device without an electrically operated pump. An active conveying unit for the liquid such as, e.g., a syringe pump or a roller pump, can be omitted when a passive transport or admixing of the liquid by pushing the liquid to the mixing unit is accomplished by pressure above atmospheric pressure and/or by suction based on the Venturi pump or jet pump principle.

In another aspect of the invention a generation device is stated, with which an aerosol can be generated. For example, the generation device may be used in a device with the inventive instrument, which inventive instrument is described herein. However, the generation device can also be used independently of the embodiments of the inventive instrument described herein. The generation device according to the invention can be used for loading an instrument with aerosol, for example for open surgery or endoscopic, in particular laparoscopic, surgery, in order to be able to dispense aerosol by means of the instrument.

The generation device comprises a mixing unit in order to mix liquid and gas with each other to produce an aerosol. The mixing unit is connected to the liquid container for supplying the mixing unit with liquid. The generation device is adapted to use the gas pressure of a gas (pressurized gas) subjected to a pressure above atmospheric pressure to pressurize the liquid in order to press the liquid out of the liquid container to the mixing unit. In doing so, the gas can directly press on the liquid surface. Alternatively, the gas may press on a container, for example a bag that contains the liquid. The gas may press against a piston or a membrane which, in turn, presses directly on the liquid or a liquid container, for example a bag.

Embodiments of the generation device according to the invention, in which a compressible liquid container, e.g., a bag that is closed up to a port for the connection to the mixing unit, is arranged in a pressurized container, have the advantage that it can be ensured that the liquid supply is independent of, for example, the orientation of the liquid container, for example the bag, or the pressurized container that contains the liquid container.

Preferably, the liquid supply is independent of the position of the liquid container. This is preferably accomplished in that there is always a minimum liquid pressure acting on the connection of the mixing unit for supplying liquid, independent of the orientation and position of the liquid container. This can be accomplished by applying pressure to the liquid.

The device is particularly simple when the generation device is connected to a stationary or mobile pressurized gas storage such as, for example, a gas bottle, or a stationary pressurized gas network, as the source for the pressurized gas. For example, $CO_2$ may be used as gas. Preferably, the source is adapted to provide gas with a pressure of a few Bar.

When the gas to be mixed with liquid to produce an aerosol and the gas that is determined to press on the liquid originate from the same gas source, it is not necessary to provide two independent gas sources (e.g., two gas bottles). Rather, one gas source (e.g., one gas bottle) is sufficient, said source delivering gas for supplying the mixing unit, as well as for charging the liquid in the liquid container with pressure.

In the embodiments, pressure from the outside is applied to a liquid container containing the liquid in order to convey the liquid to the mixing unit.

Preferably, the liquid container is adapted and intended to be compressed in order to be able to compress the liquid container due to the pressure, in order to thus press liquid out of the liquid container to the mixing unit.

For example, the liquid container may be a bag. Preferably, a standard bag is used as is available in hospitals where the generation device is used. If a standard bag is used, the filling of a special fluid container for the device may be omitted. For example, the fluid may be a sterile isotonic saline solution. For example, the bag may be an infusion bag as is commonly used in hospitals.

In the embodiments, the liquid container is arranged in a pressurized container, in which case pressure is applied to the pressurized container in order to press the liquid out of the liquid container to the mixing unit. In the pressurized container, the gas pressure of the gas can directly act on the liquid container. This makes the generation device particularly simple. Alternatively, the pressure may act, for example, on a membrane or a piston, which membrane or which piston acts on the liquid container. Or the liquid is arranged in a cylinder in one of two working chambers, which are separated from each other by a piston, in which case the other working chamber is pressurized with pressurized gas in order to press the liquid out of the working chamber by means of the piston.

In embodiments, the pressurized container itself may be the liquid container, in that the wall of the pressurized container prevents the liquid from flowing out. Pressure can be applied by the pressurized gas above the fluid level in the chamber, said gas potentially having contact with the liquid surface in order to press the liquid out of the pressurized container.

Preferably, the mixing unit works according to the Venturi pump or the jet pump principle for mixing the liquid with the gas. The mixing unit preferably comprises a channel with a constriction, in which case the channel is connected to the pressure source upstream of the constriction, and in which case the fluid container is connected to the channel downstream of the constriction and/or at the constriction. If the channel is supplied with pressurized gas upstream of the constriction, the gas flow is accelerated and the static pressure in the constriction and downstream of the constriction is decreased due to the constriction. If a fluid line is connected from the liquid container to the region with reduced static pressure to the mixing unit, the reduced static pressure promotes the loading of the channel with liquid that is drawn along by the accelerated gas in order to produce the aerosol.

A particularly simple design is attained if the channel is connected upstream of the constriction to the same pressure source of pressurized gas, which pressure source is also adapted to apply pressure to the liquid in the liquid container in order to press said liquid into the mixing unit. In particular, the channel can be connected to a pressurized gas storage (stationary or mobile) such as, for example, a gas bottle or a pressurized gas network, for example a pressurized gas network of a building, in particular a hospital building, in which case the pressurized gas storage or the pressurized gas network also is adapted to apply pressure to the fluid in the fluid container. For example, between the constriction of the channel and the pressure source, there may be provided a line branching point with two branch lines, in which case one branch line leads to the constriction and the other leads to the pressurized container. If the generation device comprises a line connected to the pressure source, said line branching between the constriction and the pressure source, in order to supply—from the line—the constriction with gas as well as provide the gas to apply pressure to the liquid, then such a branching point is preferably arranged in the mixing unit. The gas stream from the pressure source is divided into two partial streams, of which a first partial stream flows to the mixing unit and a second partial stream flows to the liquid container in order to apply pressure to the liquid by means of the second partial stream.

In a device, an instrument for dispensing aerosol via an aerosol line is connected to the generation device as described herein, in which case the proximal end of the aerosol line and the generation device remains outside the body of the patient while the instrument is being used. The proximal end of the aerosol line is connected to the generation device described herein in order to supply the instrument by means of the generation device with aerosol via the aerosol line.

BRIEF DESCRIPTION OF THE DRAWINGS

Additional features of the instrument according to the invention and the generation device according to the invention, as well as the device according to the invention, can be inferred from the dependent claims, as well as the description and the schematic figures hereinafter. They show in FIG. 1—an exemplary device according to the invention with a generation device according to the invention for the generation of an aerosol, and an instrument with a handling section according to the invention connected thereto, FIG. 2—an exemplary embodiment of a mixing unit of a generation device according to the invention as can be used, for example, in the inventive generation device as in FIG. 1, FIG. 3a—a pressurized container which contains a liquid container for use, for example, in a generation device according to the exemplary embodiment as in FIG. 1, FIG. 3b—a pressurized container which contains a liquid container for use, for example, in a generation device according to the invention according to the exemplary embodiment as in FIG. 1, FIG. 4—an exemplary embodiment of an instrument according to the invention as can be used, for example, in the exemplary embodiment of the inventive generation device as in FIG. 1.

DETAILED DESCRIPTION

Figure 1:
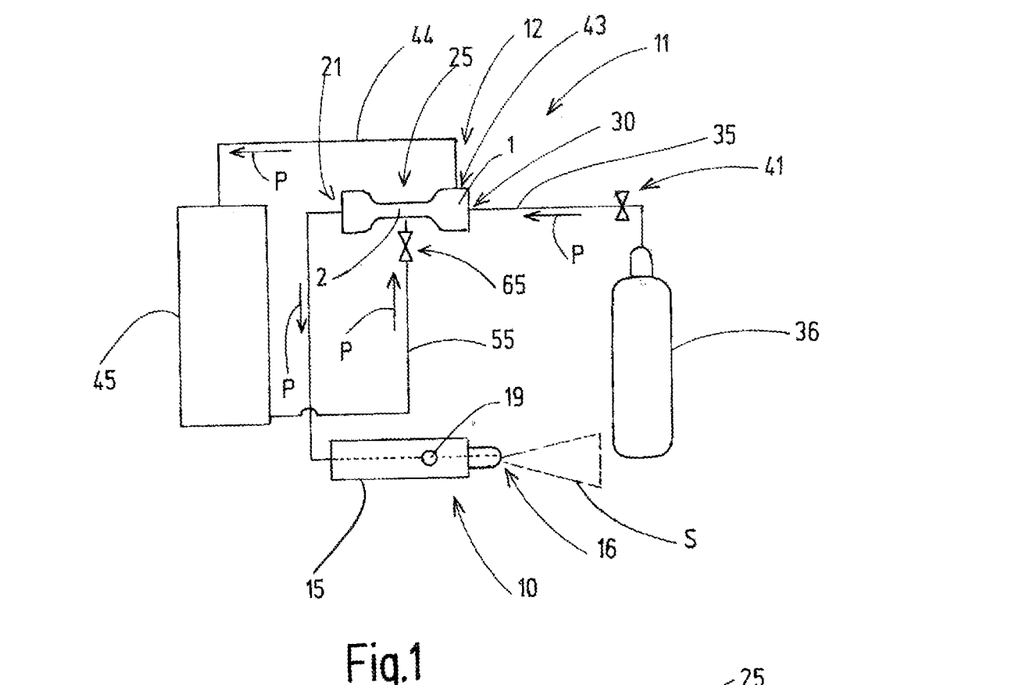

FIG. 1 shows an exemplary embodiment of a device with an exemplary embodiment of a generation device according to the invention for the generation of an aerosol and an exemplary embodiment of a medical instrument connected thereto.

Figure 4:
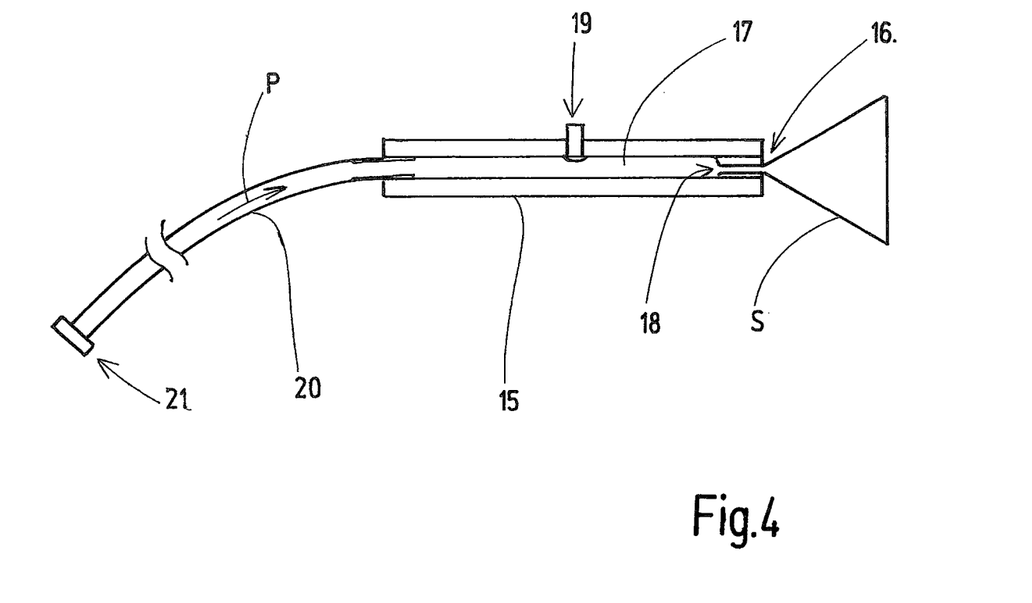

FIG. 4 shows an exemplary embodiment of the medical instrument. The medical instrument 10 may be part of a device 11 that, in addition, comprises a generation device 12 for aerosol. FIG. 1 shows exemplary device 11 according to the invention. The medical instrument 10 comprises a handling section 15 for handling the instrument 10 while a medical, in particular a surgical, procedure, is being performed. The handling section may also be referred to as handle part or applicator. The handling section 15 is preferably adapted and intended to be gripped at the handling section held by the user while the instrument 10 is being handled during the surgical procedure for orienting an aerosol outlet 16 provided on the handling section 15 in order to dispense the aerosol in a targeted manner in a desired region. A channel 17 extends in the handling section 15, which channel ends in the environment at the aerosol outlet 16 which is arranged on the distal end of the handling section 15 from which aerosol outlet an aerosol can be dispensed in the form of a full cone spray S or as a jet. The full cone spray or jet of aerosol can be used, e.g., for the preparation by forcing apart tissue structures without cutting, for moistening, preventing thermal damage by cooling or for improving sight by rinsing away liquids or by removing smoke, or for minimizing the formation of smoke. Upstream of the aerosol outlet 16, the channel 17 has a constriction 18 to form a nozzle for accelerating the aerosol stream before its discharge from the aerosol outlet 16. At least one control element 19 for operating the instrument 10 is arranged on the handling section 15, which control element can be used to block or clear the aerosol flow through the channel 17. This can be accomplished, for example, by clamping off a hose or tube by means of the control element 19 which may form the channel 17 in the handling section in order to stop the aerosol flow to the aerosol outlet 16. From the generation device 12 to the handling section 15 leads an aerosol line 20, with which the channel 17 of the handling device, and thus the aerosol outlet 16, is fluidically connected to the generation device 12. The aerosol line 12 is—at least in one section—a hose line. According to the invention, the aerosol is produced in the generation device 12 which is arranged on the proximal end 21 of the aerosol line 20. The generation device 12 forms a proximal end of the device 11. A line for the separate transport of liquid and gas to the handling section 15 for the production of aerosol there can thus be omitted.

Figure 2:
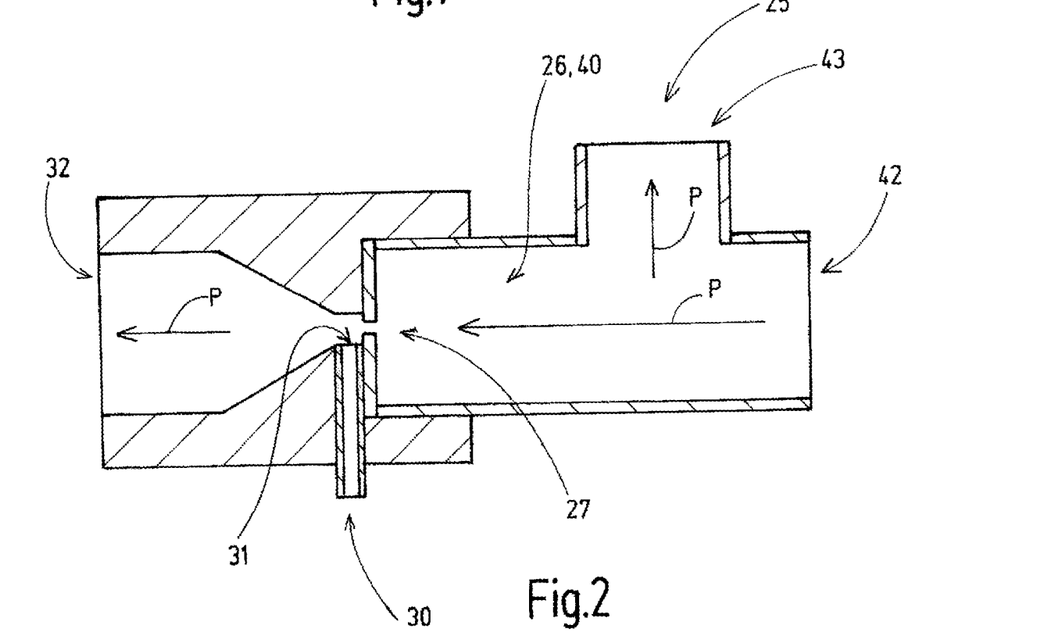

The generation device 12 preferably comprises a mixing unit 25 that contains a Venturi nozzle. FIG. 2 shows an example of a mixing unit 25 as can be used in the exemplary embodiment according to FIG. 1. The mixing unit 25 comprises a channel 26 which has a constriction 27 for forming the Venturi nozzle. For loading the channel 26 with pressurized gas upstream of the constriction 27, the mixing unit 25 has a port for pressurized gas. Downstream of the constriction 27, the channel 26 is connected to a port 30 of the mixing unit 25 for a fluid, in order to supply the channel 26 with fluid, in particular liquid. Downstream of the location 31 of the channel 26, where the fluid enters into the channel 26, the mixing unit 25 has a dispensing connection 32 for aerosol. The dispensing connection 32 is connected to the aerosol line 20, which leads to the handling section 15 and to the aerosol outlet 16 of the instrument 10.

The mixing unit 25 is connected to a source 36 for pressurized gas, in particular $CO_2$, by means of a first pressurized gas line 35, in order to load the mixing unit 25 with pressurized gas from the source 36. As shown by FIG. 1, the source 36 may be, for example, a mobile pressurized gas storage such as, for example a gas bottle, or a stationary pressure storage. Preferably, there is no pump or compressor between the pressurized gas storage 36 and the mixing unit 25, but the pressure of the pressurized gas storage 26 is sufficient for the generation of the aerosol. Between the section 40 of the channel 26, which adjoins the constriction 27 upstream, and the pressurized gas storage 36, there is a pressure-reducing device 41 for reducing the pressure from the pressurized gas storage 36. In the depicted exemplary embodiment, this is a pressure-reducing device 41, which is arranged between the pressurized gas storage 36 and the connection 42 of the mixing unit 25 for pressurized gas. The pressure-reducing device 41 is adapted to reduce the gas pressure provided by the gas bottle 36 to a few Bar in the section 40 of the channel 26, which section 40 adjoins the constriction 27 upstream. In order to branch a part of the gas off the section 40 of the channel 26 to with the part press the liquid to or into the mixing unit 25, the mixing unit 25 comprises—upstream of the constriction 27—a branching point connection 43 for branching off gas into a second pressurized gas line 44 that is fluidically connected to a container 45, which can be loaded with the pressurized gas. Consequently, the container 45 is connected—by means of the second pressurized gas line 44—to the same pressurized gas storage 36 as the mixing unit 25. The branching point 43 for loading the container 45 from the same source 36 for pressurized gas as the mixing unit 25 may, of course, alternatively also be arranged upstream of the mixing unit 25 between the mixing unit 25 and the source 36.

Embodiments of the device 11 according to the invention comprise such a container 45 (pressurized container) that can be loaded with pressurized gas. By means of the gas pressure, a fluid, in particular a saline solution contained in the pressurized container 45, is to be pressed out of the container 45 to the mixing unit 25.

Figure 3A:
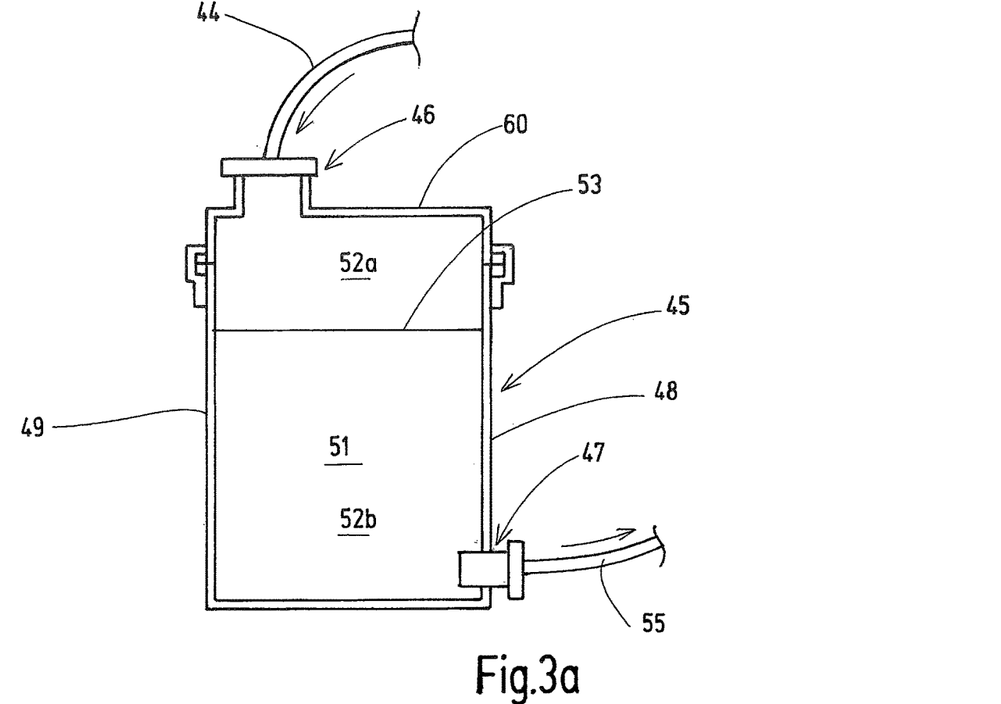

FIG. 3a shows an example of one embodiment of the pressurized container 45. The pressurized container 45 has a port 46 for loading the pressurized container with gas and a port 47 for dispensing the liquid. The port 46 for loading is connected to the second pressurized gas line 44. The wall of the pressurized container 45 itself prevents the liquid from flowing out. The pressurized container 45 according to FIG. 3a thus forms a liquid container 49, which is filled with liquid 51 to a filling level. The chamber 52 above the liquid level 53 can be loaded, via the port 46 for loading with the gas under a pressure of a few Bar, so that the gas presses directly on the liquid level 53 and thus presses the liquid 51 out of the port 47 so as to be dispensed. The port 47 used for dispensing is connected to a liquid line 55, which is connected—on the other end—to the port of the mixing unit 25 for fluid.

Figure 3B:
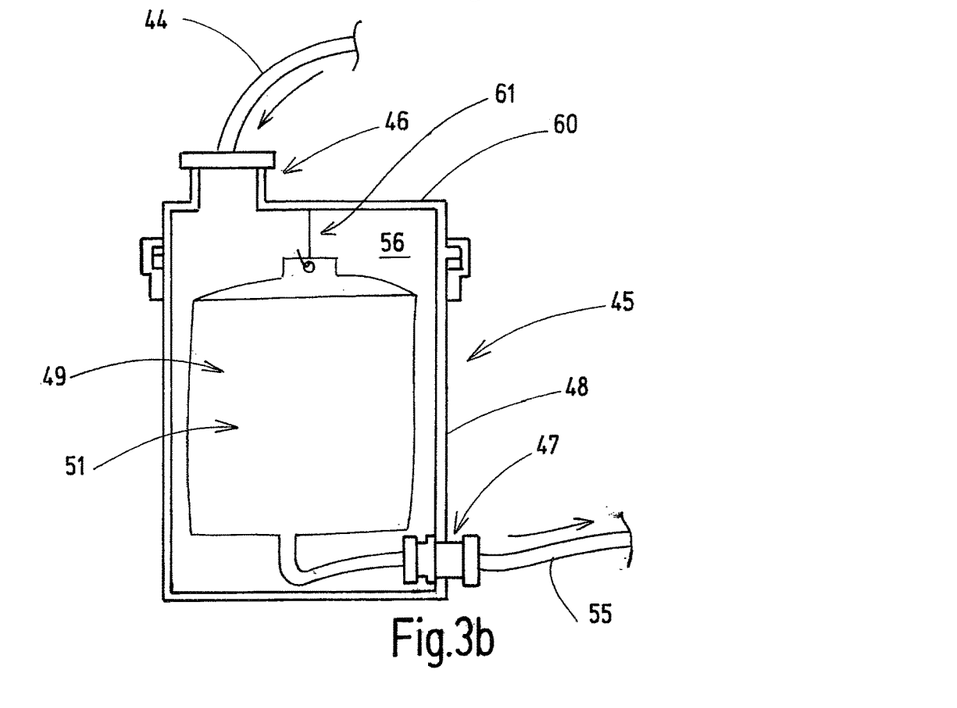

FIG. 3b shows an example of an embodiment that is an alternative to the embodiment of the pressurized container 45 according to FIG. 3a. Different from the embodiment according to FIG. 3a, the pressurized container 45 itself contains a compressible liquid container 49, for example a bag 49. The chamber 56 around the bag 49 is loaded—via the port for loading 46—with the gas having a gas pressure of a few Bar, so that the bag 49 is compressed, in which case the liquid is pressed out of the port 47 to be dispensed. For example, the bag 49 may be a standard container in particular for saline solution available in the hospital where the device 11 is used. For example, the bag is a standard infusion bag. Preferably, the port 47 for dispensing the liquid is configured consistent with a standard connecting system used in the medical field. For example, the port may be a Luer lock port consistent with the Luer system. For example, the liquid container 49 may be suspended inside the pressurized container 45 from the lid 60 of the pressurized container 48 by means of a suspension device 61. Alternatively, the pressurized container 45 may be adapted such that the fluid container 49 is placed into the pressurized container 45, which is connected to the line 35 between the gas bottle or the pressure-reducing device 41 and the section 40 of the channel 26 upstream of the constriction 27, so that the excess pressure from the gas bottle may act on the fluid container 49, in particular the bag 49. One advantage of the use of a pre-filled fluid container 49, for example of a standard bag, for example infusion bag, available in the hospital, is that the direct filling of the pressurized container 45 as the fluid container 49 may be omitted. Precautions for ensuring the sterility of the saline solution supplied to the mixing unit are simpler when a standard bag 49 with sterile isotonic saline solution for clinical applications is used.

In the exemplary embodiments that represent alternatives to the exemplary embodiments according to FIGS. 3a and 3b, it is possible, for example, for a membrane or a piston to divide the chamber of the pressurized container (not illustrated), in which case one chamber volume is filled with pressurized gas and the other chamber volume contains the fluid. Pressure is applied to the membrane or the piston by means of the pressurized gas with a force to directly apply pressure to a liquid column (as in FIG. 3a) or to the liquid container (as in FIG. 3b). Referring to the alternative exemplary embodiments, the pressurized container—as in the exemplary embodiment according to FIG. 3a—may directly form a liquid container or—as in the exemplary embodiment according to FIG. 3b—contain a flexible (compressible) liquid container.

Between the liquid container 49 and the orifice 31 in the channel 26 on the port 30 of the mixing unit 25 for the fluid, there may be arranged a throttle device 65 to reduce the pressure in the fluid line 55 between the liquid container and the orifice 31 in the channel 26. In doing so, the flow rate of the liquid can be adjusted. The greater the pressure drop generated on the throttle device 65, the lower is the flow rate of liquid. In doing so, the mixing ratio of gas and liquid can be adjusted. In the channel section 40 of the mixing unit 25 upstream of the constriction, the static pressure of the gas flow is greater than in the constriction, toward which the flow is accelerated in a flowing manner, and, consequently, the static pressure decreases.

The generation device 12 and/or the source 36 preferably are supported by the base—for example, via one or more carrying devices.

The device 11 works as follows. The flow directions in the lines and channels are identified in the Figures by arrows P next to or in the lines and channels:

The channel 26 of the mixing unit 25 is loaded with gas, for example $CO_2$, by means of the gas bottle 36, with a pressure of a few Bar, for example greater than or equal to 2 Bar, for example approximately 7 Bar. When, on the handling section 15, the passage through the line that forms the channel 17 in the handling section 25 is cleared, the gas flows through the channel 17 and the second pressurized gas line 44 into the pressurized container 45 and presses the liquid there out of the pressurized container 45 to the mixing unit 25. This may happen, in that the gas pressure acts directly on the liquid bag 49 compressing said bag (according to FIG. 3b) and thus on the liquid through the fluid line 55 to the channel 26 in the mixing unit 25, or in that the pressure acts directly on the liquid surface 53 (according to the exemplary embodiment of FIG. 3a). In the depicted and described embodiments, pressure may be applied to the liquid 51, in that the liquid container 49 is pressurized, in order to convey the liquid 51 to the mixing unit 25. With the embodiment according to FIG. 3b it is ensured that the liquid supply is independent of the orientation of the bag 49 of the pressurized container 45. When the gas flows through the Venturi nozzle, which is formed by the constriction 27 of the channel 26 of the mixing unit 25, the narrowest point of the channel 26 which forms the constriction 27 displays a maximum dynamic pressure and a minimum static pressure. When the gas flows through the channel 26 of the mixing unit 25, the gas is accelerated at the constriction 27 of the channel, in which case the static pressure decreases and thus is below the pressure inside the pressurized container 45. Consequently, the gas sucks liquid out of the liquid line 55 into the gas stream, in which case the liquid vaporizes into liquid droplets that are carried along by the gas stream. The section 40 of the channel 26 of the mixing unit 25 adjoining the constriction 27 upstream is connected, in the exemplary embodiment according to FIG. 3a, to the lower chamber 50b of the container 45 that is occupied by the saline solution. The difference between the static pressure in the constriction 27 and the pressure in the pressure container 45 has the result that the saline solution is conveyed at the constriction 27 downstream thereof in the gas stream and is mixed there with the gas stream. The pressure in the pressurized container 45 is a function of the pressure in the section 40 of the channel 26, which adjoins the constriction 27 upstream because the pressurized container 45 is connected—via the second pressurized gas line 44—to the section 40.

The thusly produced aerosol enters from the aerosol outlet of the mixing unit 25 into the aerosol line 20 and is conveyed through the channel 17 in the handling section 15 to the aerosol outlet 16 of the instrument 10 on the handling section 15 in order to be dispensed there. In the nozzle, upstream of the aerosol outlet 16 on the handling section 15—which is formed by the constriction 18—the aerosol flow is accelerated by means of the nozzle.

If, as in the described embodiments, the mixture of aerosol takes place on the proximal end 21 of the instrument 10, the continued transport of the gas-water mixture to the distal end of the handling section 15 (aerosol applicator) may occur only through an aerosol line 20, so that another line will be unnecessary. For example, the mixing unit 25 may be arranged in an apparatus, to which the instrument 10 is connected. The apparatus-side mixing unit 25, in which the gas and the fluid are joined, may have the shape of a Y, for example.

In doing so, the transport of the liquid stream may preferably take place by means of a passive transport unit, i.e., without an electrically operated pump. Preferably, there is no electrically operated pump between the liquid container 49 and the location 31 at which the fluid enters the channel 26 in the mixing unit 25, which pump would be adapted and intended to transport liquid in the channel 26 of the mixing unit 25. To do so, according to embodiments of the invention, the pressure of a pressurized gas storage 36 such as, for example, a gas bottle, is used to supply the mixing unit 25 which, additionally preferably, may form a jet pump, and, on the other hand, press the fluid out of the fluid container 49 to the mixing unit 25. Compared to a device which comprises an active transport unit for the liquid such as, e.g., a syringe pump or a roller pump, the device 11 according to the invention provides—in the embodiments in which such a pump between the liquid container 49 and the mixing unit 45 is omitted—the advantage that the cost for an active transport unit in the device can be saved. As a result of this, the device 11 according to the invention is relatively inexpensive to manufacture and maintain and thus comparatively more favorable. Furthermore, the mass flow of fluid is a function of the pressure applied in the first pressurized gas line 35. Thus, the quantity of aspirated liquid is also a function of the pressure in the first pressurized gas line 35. Therefore, the suggested transport provides self-adjustment. The stronger the suction of the jet pump is on the fluid line 55, said jet pump being formed by the mixing unit 25 having the constriction 27, the stronger the liquid is pressed out of the fluid container 49 into the fluid line 55 due to the application of pressure by the pressurized container 45.

Disclosed is a medical instrument 10 with an aerosol outlet 16, which is fluidically connected—via an aerosol line 20—to a generation device 12. The generation device 12 is adapted to generate aerosol for dispensing by means of the medical instrument 10. In addition, a generation device 12 is stated, which, in embodiments of the generation device 12, for example can be used in a device 11 with the instrument 10 according to the invention. The generation device 12 comprises a mixing unit 25 for mixing a liquid and a gas together, which mixing unit 25 is connected to a liquid container 49 for supplying the mixing unit 25 with a liquid, in which case the generation device 12 is adapted to utilize the gas pressure of a gas under pressure subjecting the liquid to a pressure in order to press the liquid out of the liquid container 49 to the mixing unit 25.

| | List of Reference Signs |
|---|---|
| 10 | Medical instrument |
| 11 | Device |
| 12 | Generation device |
| 15 | Handling section |
| 16 | Aerosol outlet |
| 17 | Channel |
| 18 | Constriction |
| 19 | Control element |
| 20 | Aerosol line |
| 21 | Proximal end |
| 25 | Mixing unit |
| 26 | Channel of the mixing unit |
| 27 | Constriction of the channel of the mixing unit |
| 30 | Port |
| 31 | Location/orifice |
| 32 | Dispensing connection |
| 35 | First pressurized gas line |
| 36 | Source/pressurized gas storage/gas bottle |
| 40 | Section |
| 41 | Pressure-reducing device |
| 42 | Connection |
| 43 | Branching point connection/branching point |
| 44 | Second pressurized gas line |
| 45 | Container/pressurized container |
| 46 | Port |
| 47 | Port |
| 48 | Wall of the pressurized container |
| 49 | Liquid container/bag |
| 51 | Liquid |
| 52a | Chamber |
| 52b | Chamber |
| 53 | Liquid level |
| 55 | Liquid line |
| 56 | Chamber |
| 60 | Lid |
| 61 | Suspension device |
| 65 | Throttle device |
| S | Full cone spray aerosol |
| P | Arrow |

The invention claimed is:

1. A system for generating and dispensing an aerosol, the system comprising:
    a generation device (12) configured to generate an aerosol by vaporizing a liquid with a pressurized gas from a pressurized gas source (36), the generation device (12) comprising a mixing unit (25) for mixing the liquid and the pressurized gas together;
    a pressurizable container (45) configured to be loaded with the pressurized gas;
    a liquid container (49) in the form of a compressible bag fluidly connected to the mixing unit (25) for supplying the mixing unit (25) with the liquid;
    wherein the generation device (12) is adapted to utilize the pressurized gas to apply pressure to the pressurizable container (45) for expelling the liquid out of the liquid container (49) into the mixing unit (25); and
    a medical instrument (10) including an aerosol outlet (16) for dispensing the aerosol generated by the generation device (12) onto or into a patient, wherein the medical instrument (10) is fluidically connected to the generation device (12) by an aerosol line (20) for supplying the aerosol to the medical instrument (10);

wherein the mixing unit (25) has a channel (26) with a constriction (27), wherein the channel (26) is configured to be connected to the pressurized gas source (36) upstream of the constriction (27) for supplying the pressurized gas to the mixing unit (25), wherein the liquid container (49) is connected to the channel (26) at the constriction (27) and/or downstream of the constriction (27), in order to convey the liquid out of the liquid container (49) into the channel (26) via a reduction of pressure in the channel (26) induced by the pressurized gas flowing through the constriction;

wherein the mixing unit (25) comprises a T-connector, wherein the constriction (27) is located at a first port of the T-connector, a second line (44) extends between a second port of the T-connector and the pressurizable container (45), and a third port of the T-connector is configured to be connected to the pressurized gas source (36), such that, in use, the pressurized gas source (36) supplies the constriction (27) with the pressurized gas, as well as provides the pressurized gas for applying positive pressure to the liquid.

2. The system according to claim 1, wherein the generation device (12) is configured to be connected to the pressurized gas source (36), wherein the pressurized gas source (36) comprises a gas bottle (36) or a stationary pressurized gas network.

3. The system according to claim 1, wherein the pressurized gas is configured to act directly on the liquid container (49) to compress the liquid container (49).

4. The system according to claim 1, wherein the channel (26) is connected, upstream of the constriction (27), to the pressurized gas source (36), which the generation device (12) is configured to use to apply positive pressure to the liquid.

5. The system according to claim 1, wherein the liquid container (49) is suspended within the pressurizable container (45).

6. The system according to claim 1, wherein the compressible bag contains a saline solution.

7. The system according to claim 1, wherein the compressible bag is connected to the mixing unit (25) via a Luer lock port for dispensing the liquid in the compressible bag.

8. The system according to claim 1, wherein the compressible bag includes an interior configured to hold the liquid therein and an opening that is not in communication with the interior to allow the compressible bag to be hung therefrom.

9. The system according to claim 1, wherein the generation device (12), the pressurizable container (45) and the liquid container (49) are remote from the medical instrument (10) such that the generation device (12), the pressurizable container (45) and the liquid container (49) are not supported by the medical instrument (10).

10. A system for generating and dispensing an aerosol, comprising:

a generation device (12) for generating an aerosol including a mixing unit (25) for mixing a liquid and a pressurized gas from a pressurized gas source (36) together to form the aerosol, wherein the mixing unit (25) is connected to a liquid container (49) for supplying the mixing unit (25) with the liquid, wherein the generation device (12) is adapted to utilize the pressurized gas to apply pressure to the liquid for expelling the liquid out of the liquid container (49) into the mixing unit (25);

wherein the liquid container (49) is a compressible bag hung from a suspension device within a pressurizable container (45), and wherein the pressurizable container (45) is operably connected to the generation device (12) for receiving the pressurized gas to pressurize the pressurizable container (45); and a medical instrument having an aerosol outlet (16) for dispensing the aerosol generated by the generation device (12) onto or into a patient, wherein the medical instrument (10) is fluidically connected to the generation device (12) by an aerosol line (20);

wherein the mixing unit (25) has a channel (26) with a constriction (27), wherein the channel (26) is configured to be connected to the pressurized gas source (36) upstream of the constriction (27) for supplying the pressurized gas to the mixing unit (25), wherein the liquid container (49) is connected to the channel (26) at the constriction (27) and/or downstream of the constriction (27), in order to convey the liquid out of the liquid container (49) into the channel (26) via a reduction of pressure in the channel (26) induced by the pressurized gas flowing through the constriction;

wherein the mixing unit (25) comprises a T-connector, wherein the constriction (27) is located at a first port of the T-connector, a second line (44) extends between a second port of the T-connector and the pressurizable container (45), and a third port of the T-connector is configured to be connected to the pressurized gas source (36), such that, in use, the pressurized gas source (36) supplies the constriction (27) with the pressurized gas, as well as provides the pressurized gas for applying positive pressure to the liquid.

11. The system according to claim 10, wherein the channel (26) is connected upstream of the constriction (27) to the pressurized gas source (36), which the generation device (12) is configured to use to apply positive pressure to the liquid.

12. The system according to claim 10, wherein the compressible bag includes a closed end and an opening adjacent the closed end for allowing the compressible bag to be hung therefrom.

13. The system according to claim 12, wherein the compressible bag includes an opening at an opposite end from the closed end for dispensing the liquid therefrom.

14. The system according to claim 10, wherein the pressurizable container (45) comprises a Luer lock port for dispensing the liquid in the compressible bag.

15. The system according to claim 10, wherein the suspension device is a hook.

16. The system according to claim 10, wherein the generation device (12), the pressurizable container (45) and the liquid container (49) are remote from the medical instrument (10) such that the generation device (12), the pressurizable container (45) and the liquid container (49) are not supported by the medical instrument (10).

* * * * *